United States Patent [19]

Appleton et al.

[11] 4,057,641
[45] Nov. 8, 1977

[54] METHOD OF TREATING INFLAMMATION WITH 2-(2,3-DIHYDRO-2-ISOPROPYL-4-OXO-4H-1-BENZOPYRAN-6-YL)PROPIONIC ACID

[75] Inventors: Richard Anthony Appleton; Kevan Brown, both of Loughborough, England

[73] Assignee: Fisons Limited, London, England

[21] Appl. No.: 557,897

[22] Filed: Mar. 12, 1975

[30] Foreign Application Priority Data

Mar. 22, 1974 United Kingdom ............ 12784/74

[51] Int. Cl.$^2$ ............... A61K 31/35; C07D 311/72
[52] U.S. Cl. ........................ 424/283; 260/345.5; 260/520 R; 260/520 C; 260/590 B; 260/613 D; 560/53; 560/55
[58] Field of Search ............... 260/345.2; 424/283

[56] References Cited

U.S. PATENT DOCUMENTS

| | | | |
|---|---|---|---|
| 2,897,211 | 10/1956 | Da Re | 260/345.2 |
| 3,598,840 | 10/1971 | Majoie | 260/345.2 |
| 3,770,802 | 11/1973 | Sianesi | 260/345.2 X |
| 3,775,435 | 11/1973 | Sellstedt | 260/345.2 |
| 3,825,574 | 7/1974 | Brown | 260/345.2 |
| 3,862,143 | 1/1975 | Klutchko et al. | 260/345.2 |
| 3,912,760 | 10/1975 | Kaminsky | 260/345.2 X |
| 3,931,205 | 1/1976 | Nakanishi et al. | 260/345.2 |

OTHER PUBLICATIONS

Matshoka et al., Chem. Abst., vol. 53, 5257(i), 1959, citing Nippon Kagaku Zasshi, 78, pp. 651-653, (1957).

Patel, et al., Chem Abst., vol. 79, 136943y (1973), citing J. Indian Chem. Soc., 50, pp. 295-298 (1973).

Paolo Da Re, et al., Chem. Abst., 53, 21923(h), 1959, citing Ann. Chim. (Rome) 48, pp. 762-769 (1958).

*Primary Examiner*—Bernard Helfin
*Assistant Examiner*—G. T. Breitenstein
*Attorney, Agent, or Firm*—Merriam, Marshall, & Bicknell

[57] ABSTRACT

There are described compounds of formula I,

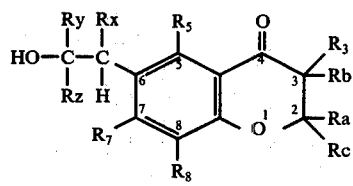

in which
- Ra is hydrogen, alkyl, alkenyl or phenyl,
- $R_3$, $R_5$, $R_7$ and $R_8$, which may be the same or different, are each hydrogen, alkyl, alkoxy, halogen, hydroxy, alkenyl or phenyl,
- Rx is hydrogen or alkyl,
- Ry and Rz are both hydrogen, or together represent a carbonyl oxygen atom,
- Rb and Rc are both hydrogen or together represent a carbon-carbon bond, and pharmaceutically acceptable derivatives thereof. There are also described processes for making the compounds and pharmaceutical, e.g. anti-inflammatory compositions, containing the compounds.

1 Claim, No Drawings

METHOD OF TREATING INFLAMMATION WITH 2-(2,3-DIHYDRO-2-ISOPROPYL-4-OXO-4H-1-BENZOPYRAN-6-YL)PROPIONIC ACID

This invention relates to new compounds, methods for their preparation and compositions containing them.

According to our invention we provide compounds of formula I,

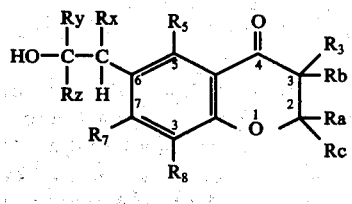

in which
- Ra is hydrogen, alkyl, alkenyl or phenyl,
- $R_3$, $R_5$, $R_7$ and $R_8$, which may be the same or different, are each hydrogen, alkyl, alkoxy, halogen, hydroxy, alkenyl or phenyl,
- Rx is hydrogen or alkyl,
- Ry and Rz are both hydrogen, or together represent a carbonyl oxygen atom,
- Rb and Rc are both hydrogen or together represent a carbon-carbon bond, and pharmaceutically acceptable derivatives thereof.

According to our invention we also provide a process for the production of a compound of formula I, or a pharmaceutically acceptable derivative thereof, which comprises a. producing a compound of formula Ia,

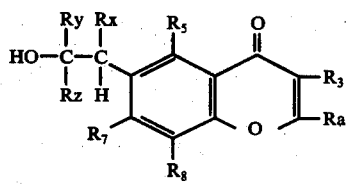

in which Ra, Rx, Ry, Rz, $R_3$, $R_5$, $R_7$ and $R_8$ are as defined above, by cyclising a compound of formula II,

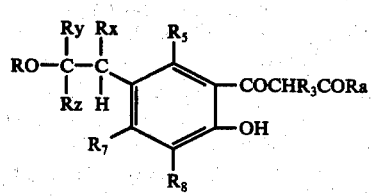

in which Ra, Rx, Ry, Rz, $R_3$, $R_5$, $R_7$, and $R_8$ are as defined above, and R is hydrogen or an alcoholic residue when Ry and Rz together represent carbonyl oxygen, and R is hydrogen when Ry and Rz are both hydrogen, b. producing a compound of formula Ib,

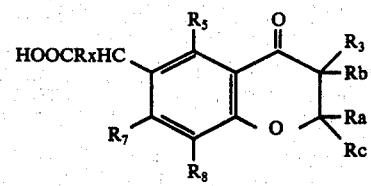

in which Ra, Rb, Rc, Rx, $R_3$, $R_5$, $R_7$ and $R_8$ are as defined above, by (i) selectively oxidising a corresponding compound of formula Ic,

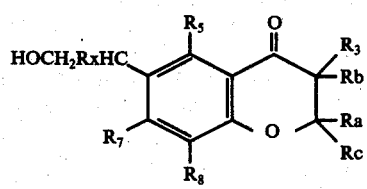

in which Ra, Rx, Rb, Rc, $R_3$, $R_5$, $R_7$ and $R_8$ are as defined above, or (ii) hydrolysing a corresponding ester of a compound of formula Ib, c. producing a compound of formula Id,

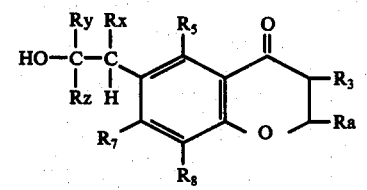

or an ester thereof,
in which $R_3$, $R_5$, $R_7$, $R_8$, Ra, Rx, Ry and Rz are as defined above, by selective reduction of a corresponding compound of formula Ia, or an ester thereof, d. cyclising a compound of formula VII,

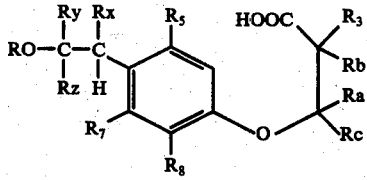

in which R, $R_3$, $R_5$, $R_7$, $R_8$, Ra, Rb, Rc, Rx, Ry and Rz are as defined above, or e. producing a compound of formula Id by cyclising a compound of formula VIII,

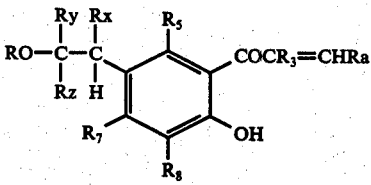

in which $R_3$, $R_5$, $R_7$, $R_8$, Ra, Rx, Ry, Rz and R are as defined above, and where desired or necessary converting the compound of formula I to a pharmaceutically acceptable derivative thereof, or vice versa.

Process (a) may be carried out by heating, or under basic or neutral conditions. It is however preferred to carry out the cyclisation is the presence of an acid, e.g. hydrochloric acid, and in a solvent which is inert under the reaction conditions, e.g. a lower alkanol such as ethanol, or a water miscible ether such as dioxan or tetrahydrofuran. The reaction may be carried out at from about 20° to 150° C. When a compound of formula II in which R is an alcoholic residue is used as starting material, the alcoholic residue is usually removed during the cyclisation, however the product in which the alcoholic residue is still present may, if desired, be separated and used as such or may be further hydrolysed to the free acid. Suitable alcoholic residues include those containing up to an including 10 carbon atoms, e.g. a lower alkyl group or a benzyl group.

Process (b)(i) may be carried out using a suitable selective oxidising agent known to oxidise a —CH$_2$OH group to a —COOH group. Thus for example a suitable oxidising agent comprises an aqueous mixture of chromium trioxide and sulphuric or acetic acid. The reaction may be carried out in a water miscible organic solvent, e.g. acetone, at a temperature of from about 10° to 30° C. The oxidation passes through the corresponding aldehyde which is usually present in the reaction mixture in the form of a metal complex and which is usually not isolated.

Process (b)(ii) may be carried out using conventional techniques, for example under mildly basic conditions, e.g. using sodium carbonate, sodium bicarbonate or sodium hydroxide, or under acidic conditions, e.g. a mixture of aqueous dioxan and hydrochloric acid. The ester may be any suitable ester of the —CHRx COOH group, e.g. an ester derived from an alcohol containing up to and including 10 carbon atoms, e.g. a lower alkyl or a benzyl ester.

Process (c) may be carried out using conventional techniques, e.g. by catalytic hydrogenation using a Raney nickel or a palladium (e.g. 5% Pd on BaSO$_4$) catalyst at a temperature of from about 20° to 50° C at a pressure of from about 20 to 100 psi.

The cyclisation of process (d) may be carried out by treating the appropriate compound of formula VII with a cyclising agent, for example a dehydrating agent such as chlorosulphonic, polyphosphoric or sulphuric acid. The reaction is preferably carried out under anhydrous conditions and may be carried out at a temperature of from about 0° to 100° C. Alternatively cyclisation may be achieved by converting the free carboxy group of the compound of formula VII to an acyl halide group and subjecting the resulting acyl halide to an intramolecular cyclisation reaction.

The cyclisation of process (e) may be carried out under acidic, or preferably basic conditions, e.g. in the presence of an aqueous alkali metal hydroxide such as sodium hydroxide. The reaction may also be carried out in the presence of a water miscible solvent, e.g. a lower alkanol such as ethanol. The reaction is preferably carried out at a temperature of from about 10° to 60° C.

Compounds of formula II may be made by reacting a compound of formula IV,

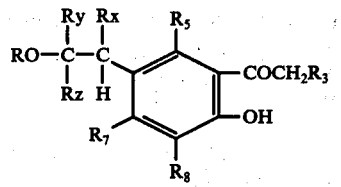

in which R, Rx, Ry, Rz, R$_3$, R$_5$, R$_7$ and R$_8$ are as defined above,
with a compound of formula V,

ROOC—Ra V in which R and Ra are as defined above, under conditions conventionally used in similar reactions.

Compounds of formula IV may be made from known compounds using conventional techniques known per se, for example using Friedel-Crafts reaction conditions and reacting an appropriately substituted acyl chloride with a compound of formula VI,

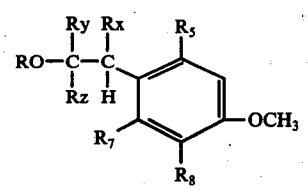

in which R, Rx, Ry, Rz, R$_5$, R$_7$, and R$_8$ are as defined above, and where necessary hydrolysing the resulting product.

Compounds of formula VII may be made by reacting a compound of formula X,

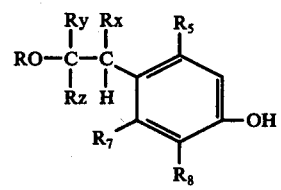

in which R, Rx, Ry, Rz, R$_5$, R$_7$ and R$_8$ are as defined above,
with a compound of formula (ROOC)RbR$_3$C-CXRaRc or of formula (ROOC)RbC═CRaRc, in which formulae R, Ra, Rb, Rc and R$_3$ are as defined above and X is a halogen atom. This reaction may be carried out under basic conditions and may, if necessary, be followed by hydrolysis of the ester group. Compounds of formula VII in which Rb and Rc are both hydrogen may be made by reduction of a corresponding compound of formula VII in which Rb and Rc together form a carbon-carbon bond, e.g. using sodium amalgam.

Compounds of formula VIII may be made by reacting a compound of formula VI with a compound RaCH═CR$_3$COCl in which Ra and R$_3$ are as defined above. The reaction may be carried out in the presence of a Friedel-Crafts catalyst, e.g. titanium tetrachloride, in a chlorinated hydrocarbon solvent, e.g. tetrachlorethane or dichloromethane, at a temperature of about −15° C. The ether —OCH$_3$ group may then be cleaved. e.g. by the addition of boron trichloride.

Compounds of formulae V, VI and X are either known or may be made from known compounds using techniques known per se.

The compounds of formula I and intermediates therefore may be isolated and purified using techniques known per se, e.g. crystalisation. Those of the compounds of formula I which are acidic may be purified by conversion to a suitable, e.g. an amine, salt; recrystalisation of the salt and regeneration of the free acid by treatment of the salt with a suitable acid.

Pharmaceutically acceptable derivatives of the compounds of formula I include pharmaceutically acceptable salts, esters and amides of those compounds in which Ry and Rz together form a carbonyl oxygen atom. Suitable salts include ammonium, alkali metal (e.g. sodium, potassium and lithium) and alkaline earth metal salts (e.g. calcium or magnesium), and salts with suitable organic bases, e.g. salts with lower alkylamines such as methylamine or ethylamine, with substituted lower alkylamines, e.g. hydroxy substituted alkylamines or with simple monocyclic nitrogen heterocyclic compounds, e.g. piperidine or morpholine. Suitable esters include simple esters derived from alcohols containing up to and including 10 carbon atoms, e.g. lower alkyl esters. The esters may be made by conventional techniques, e.g. esterification, transesterification or reaction of the acid, or a salt thereof, with an appropriate compound containing a good leaving group. The salts may be made by basification of the free acid, basic hydrolysis of an ester or by a metathetical process. The amides may be made by reaction of a corresponding ester, e.g. a lower alkyl ester, with ammonia or with an appropriate amine, e.g. a mono - or di-alkyl Cl to 6 amine.

The compounds of formula I, and pharmaceutically acceptable derivatives thereof, are useful because they possess pharmacological activity in animals. In particular the compounds are useful as anti-inflammatory agents as indicated by the carrageenan-induced edema test in rats (C A Winter et al, Proc. Soc. Exp. Biol. Vol. 111, page 544, 1962). The compounds are therefore useful in the treatment of painful inflammation of the joints and periarticular tissue such as occurs in rheumatoid arthritis, Stil's disease, osteoarthritis, various types of non-specific inflammatory or rheumatic conditions affecting the fibro muscular tissue and connective tissue and rheumatic fever and its sequelae. In those cases in which the above conditions include pain, pyrexia, and puritis, coupled with inflammation, the present compounds are useful for the relief of these associative conditions as well as the principal condition.

For the above mentioned uses the dosage administered will, of course, vary with the compound employed, the mode of administration and the treatment desired. However, in general satisfactory results are obtained when the compounds are administered at a daily dosage of from about 0.1 mg to about 20 mg per kg of animal body weight, preferably given in divided doses 1 to 4 times a day or in sustained release form. For man the total daily dose is in the range of from about 7.0 mg to about 1,400 mg and unit dosage forms suitable for oral administration comprise from about 2.0 mg to about 1,400 mg of the compound admixed with a solid or liquid pharmaceutical carrier or diluent.

The compounds of formula I, and pharmaceutically acceptable derivatives thereof, may be used on their own or in the form of appropriate medicinal preparations for enteral, parenteral or topical administration. Thus the new compounds may be worked up with inorganic or organic, pharmaceutically acceptable adjuvants, diluents or carriers. Examples of such adjuvants, diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes. We prefer the composition to be in a form suitable for oral administration. We also prefer the composition to contain up to 50% and more preferably up to 25% by weight of the compound of formula I, or of the pharmaceutically acceptable derivative thereof.

It is well known that many anti-inflammatory agents currently in use have unwanted gastro-intestinal side effects. The compounds of the present invention have, in general, been found in animal tests to have a lower incidence of side effects than some other anti-inflammatory agents.

Some of the compounds of formula I have one or more asymmetric carbon atoms and may therefore exist in the form of two or more (depending on the number of asymmetric carbon atoms) optical isomers, or a racemic or other mixtures of such isomers. The various optical isomers may be resolved, wholly or partially, using conventional techniques, e.g. formation of a salt of an acidic compound of formula I with an optically active base, e.g. cinchonidine, fractional crystalisation of the salt and subsequent regeneration of the free acid.

We prefer each of Ra, Rx, $R_3$, $R_5$, $R_7$ and $R_8$ to contain up to 10, and preferably up to 6 carbon atoms. In particular we prefer Ra to comprise a chain of 2 atoms other than hydrogen, such a chain optionally being substituted by alkyl on the atom adjacent to the chromone or chromanone nucleus. Thus Ra may be straight or branched alkyl C 1 to 4. Specific examples of Ra which may be mentioned are methyl, ethyl, iso-propyl, n-propyl, phenyl and hydrogen. Preferred values for $R_3$ are hydrogen and alkyl, e.g. methyl. We also prefer each of $R_5$, $R_7$ and $R_8$ to be selected from hydrogen, hydroxy, alkoxy, alkyl and halogen, e.g. to be hydrogen, hydroxy, methoxy, ethyl or chlorine. We particularly prefer each of $R_5$, $R_7$ and $R_8$ to be hydrogen. We prefer Rx to contain up to and including 2 carbon atoms, e.g. to be methyl. We also prefer Ry and Rz to together form a carbonyl oxygen atom (i.e. we prefer acetic acid derivatives), and Rb and Rc both to represent hydrogen (i.e. chromanone compounds).

The invention is illustrated but in no way limited by the following Examples.

EXAMPLE 1

2-(2-Ethyl-4-oxo-4H-1-benzopyran-6-yl)ethan-1-ol a. 2-(3-Acetyl-4-hydroxyphenyl)ethyl acetate Aluminum chloride (90g) was added portionwise to a stirred solution of 4-methoxyphenethyl alcohol (29.2g) and acetyl chloride (40 mls) in 1,1,2,2-tetrachloroethane (300 mls), cooled in an ice-bath, at a rate sufficient to maintain the temperature between 0° and +5° C. The mixture was stirred at room temperature for 22 hours before pouring on to crushed ice and separating the two phases. The aqueous phase was extracted with ether (3x) and the combined organic extracts were washed with water, saturated brine solution, and dried over anhydrous magnesium sulphate. Evaporation of the solvent yielded the crude product as a pale yellow oil. Vacuum distillation furnished a colourless oil bp 120°–121°/0.15 mm (35.7g; 83%)

The i.r. spectrum showed carbonyl bands at 1648 and 1742 cm$^{-1}$.

b. 3-Acetyl-4-hydroxyphenethyl alcohol

A solution of 2-(3-acetyl-4-hydroxyphenyl)ethyl acetate (35.7g) in ethanol (400 ml), and sodium bicarbonate (42g) in water (200 mls) was refluxed for 8½ hours. The ethanol was removed on a 'Rotavapor' and the residue was extracted with ether (3x). The combined ethereal extracts were washed with water, sodium bicarbonate solution, saturated brine solution, dried over anhydrous magnesium sulphate, and evaporated to yield a red oil (31.3g). The oil was recrystallised from hexane and ether (4:1) to yield the product as a pale yellow crystalline solid (18.3g). The mother liquors were concentrated and an additional batch of product was obtained as a pale yellow crystalline solid (9.3g).

The i.r. spectrum showed a carbonyl band at 1645 cm$^{-1}$.

c. 2-(2-Ethyl-4-oxo-4H-1-benzopyran-6-yl)ethan-1-ol

Sodium hydride (14.4g; 50% dispersion in oil) was washed free from oil by decantation with dry ether (3x) and hexamethylphosphoramide (30 ml) was added. 2-(3-Acetyl-4-hydroxyphenyl)ethanol (9g) in dry hexamethylphosphoramide (85 mls) was added to the resulting stirred slurry at a rate sufficient to maintain the temperature between +20° and +25° C. When evolution of hydrogen had ceased, ethyl propionate (10.2g) was added and the green solution was stirred at room temperature for 4 hours. Water was then added followed by dilute hydrochloric acid. The product was extracted with ether and washed with a small amount of water. The combined aqueous solutions were saturated with sodium chloride and re-extracted with ether. The combined ethereal solutions were dried over anhydrous magnesium sulphate and evaporation of the solution yielded 2-/ 4-hydroxy-3-(3-oxapentanoyl)phenyl /ethanol as a red oil. The red oil was refluxed in ethanol (50 mls) and concentrated hydrochloric acid (20 mls) for 1 hour. The ethanol was removed on a 'Rotavapor' and the residue was extracted with chloroform (3x). The chloroform solution was dried over anhydrous magnesium sulphate and evaporated to yield a red oil. The oil was dissolved in hot benzene, charcoaled and recrystallised from benzene and n-hexane (1:4) to yield the product as an off-white solid (4.1g) mp 75°-76° C.

Found: C, 71.5% H, 6.5%;
$C_{13}H_{14}O_3$ requires: C, 71.5% H, 6.7%

IR, NMR and MS were consistent with the proposed structure. The i.r. carbonyl absorption was at 1660 cm$^{-1}$.

EXAMPLE 2

(2-Ethyl-4-oxo-4H-1-benzopyran-6-yl)acetic acid

Jones Reagent was prepared by adding concentrated sulphuric acid (11.5 mls) carefully to a solution of chromium trioxide (13.4g) in water (20 ml). When cool, the mixture was diluted to a volume of 50 mls with water to yield a clear deep red solution.

This red solution was added dropwise to a stirred solution of 2-(2-ethyl-4-oxo-4H-1-benzopyran-6-yl)ethan-1-ol (3.5g) in acetone (30 mls) maintained at 20° C until a permanent red colouration was obtained. The reaction was stirred at room temperature for a further 1½ hours. Water was added and the product was extracted with ether (3x). The separated ethereal solution was extracted with sodium bicarbonate which was washed with water, acidified with dilute hydrochloric acid and extracted with chloroform. The chloroform solution was washed with a small volume of saturated brine solution and dried over anhydrous magnesium sulphate. Evaporation of the solvent yielded the product as an off-white solid (2.2g). Recrystallisation from benzene yielded pale yellow needle crystals mp 171°-172° C (1.1g). The mother liquors were concentrated and a second crop was obtained as a pale yellow solid (0.6g).

Found: C, 67.0%; H, 5.3%
$C_{13}H_{13}O_4$ requires: C, 67.3; H, 5.2%

Nmr, ir and ms consistent with the proposed structure.

EXAMPLE 3

2-(2-Ethyl-4-oxo-4H-1-benzopyran-6-yl)propan-1-ol a. Methyl 2-(4-methoxyphenyl propionate

Sodium hydride (6.2g; 0.258 mol) was suspended in dry hexamethylphosphoramide (45 ml) and 4-hydroxyphenylacetic acid (12.4g; 0.0815 mol), dissolved in hexamethylphosphoramide (100 ml), was slowly added to the stirred slurry so that the temperature was at 15° ± 5° C. The solution was stirred for 75 mins then methyl iodide (35 ml; 79.5g; 0.56 mol) was added at a rate sufficient to maintain the temperature below 28°. Stirring at ambient temperature was then continued for 15 hours. Water (400 ml) and 10% hydrochloric acid (400 ml) were added and the mixture was extracted with ether (2 × 300 ml). The combined ether extracts were washed with saturated sodium bicarbonate solution, with water until neutral, and then dried over magnesium sulphate. Evaporation of the solvent gave a pale yellow oil. (15.8g). The nmr spectrum showed methyl absorption at τ6.33 and 6.49 (singlets) and at τ8.62 (doublet, J = 6 cps). The ir spectrum showed a carbonyl absorption at 1740 cm$^{-1}$.

b. 2-(4-Methoxyphenyl)propan-1-ol

Methyl 2-(4-methoxyphenyl)propionate (11.39g; 0.0586 mol) was dissolved in dry ether (25 ml) and slowly added to a stirred suspension of lithium aluminium hydride (4.59g; 0.121 mol) in dry ether (60 ml); the temperature was maintained below 25° C by cooling. Stirring at ambient temperature was continued for 1 hour. Water was cautiously added dropwise to decompose the unreacted lithium aluminium hydride and the inorganic salts were dissolved by the addition of dilute hydrochloric acid. The ether was separated and the aqueous phase re-extracted with ether (2 × 100 ml). The combined ether extracts were washed with water, saturated sodium bicarbonate solution, water, and then dried over magnesium sulphate. The product was isolated as a pale yellow oil (8.72g) following evaporation of the solvent.

The n.m.r. spectrum showed methyl absorption at τ6.35 (singlet) and at τ8.85 (doublet J = 6 cps); it showed the CH$_2$OH absorption at τ6.60 (doublet J = 8 cps).

c. 2-(3-Acetyl-4-hydroxyphenyl)propyl acetate 2-(4-Methoxyphenyl)propan-1-ol (17.45g; 0.106 mol) and acetyl chloride (23 ml; 25.3g; 0.323 mol) were dissolved in 1,1,2,2-tetrachloroethane (250 ml). Aluminum chloride (60.0g; 0.451 mol) was added batchwise with stirring at a rate sufficient to maintain the temperature below 35° C. Stirring was continued at ambient temperature for 18 hours. The reaction mixture was poured into iced saline solution and extracted with ether (2 × 600 ml). The combined ether extracts were washed with saturated sodium bicarbonate solution, brine, and then dried over magnesium sulphate. The solvent was removed in vacuo leaving the product (20.05g; 80% yield) as a pale brown oil.

The ir spectrum showed carbonyl absorptions at 1640 and 1740 cm$^{-1}$.

d. 2-(3-Acetyl-4-hydroxyphenyl)propan-1-ol 2-(3-Acetyl-4-hydroxyphenyl)propyl acetate (20.0g; 0.0847 mol) and sodium bicarbonate (25.4g; 0.31 mol) were dissolved in ethanol (200 ml) and water (150 ml), and the mixture was refluxed for 20 hours. Ethanol was removed in vacuo and the residue was extracted with ether (3 × 150 ml). The combined ether extracts were washed with water, saturated sodium bicarbonate solution, brine, and then dried over magnesium sulphate. The product, after removing solvent, was chromatographed on silica gel using ether as eluent to give a pale brown oil (15.0g; 72% yield).

The i.r. spectrum showed a carbonyl band at 1642 cm$^{-1}$.

e. 2-(2-Ethyl-4-oxo-4H-1-benzopyran-6-yl)propan-1-ol 2-(3-Acetyl-4-hydroxyphenyl)propan-1-ol (15.0g; 0.077 mol) was dissolved in hexamethylphosphoramide (150 ml) and slowly added to a stirred slurry of sodium hydride (10.0g; 0.417 mol) in hexamethylphosphoramide (40 ml) at a rate sufficient to maintain the temperature below 25° C. Ethyl propionate (20.0g; 0.2mol) was added and the mixture stirred for 2 hours before pouring into 2N hydrochloric acid (600 ml). The solution was extracted with ether (2 × 300 ml) and the extracts evaporated to give 2-[4-hydroxy-3-(3-oxapentanoyl)-phenyl]propan-1-ol as a yellow oil. This was dissolved in ethanol (100 ml) containing concentrated hydrochloric acid (20 ml) and the solution was refluxed for 30 mins. The ethanol was removed in vacuo and the aqueous phase extracted with chloroform (2 × 150 ml). The combined extracts were washed with saturated sodium bicarbonate solution and dried over magnesium sulphate. The solvent was removed and the resulting oil was chromatographed on a silica gel column using ether as eluent. Recrystallisation of the product using hexane/ether (2:1) furnished a white microcrystalline solid (5.0g) mp 59.5-60.5° C.

$C_{14}H_{16}O_3$ requires: C, 72.5%, H, 6.9%
Found: C. 72.8%, H. 7.1%

EXAMPLE 4

2-(2-Ethyl-4-oxo-4H-1-benzopyran-6-yl)propionic acid 2-(2-Ethyl-4-oxo-4H-1-benzopyran-6-yl)propan-1-ol (3.0g; 0.0129 mol) was dissolved in acetone (20 ml) and Jones Reagent (Example 2) was slowly added until the solution attained a permanent brown colour. Water (100 ml) was added and the mixture was extracted with chloroform (4 × 70 ml). The combined chloroform phases were extracted with saturated sodium bicarbonate solution (4 × 30 ml). The aqueous phases were combined, washed with chloroform (100 ml) and then acidified with concentrated hydrochloric acid. The precipitated product was extracted with chloroform (3 × 100 ml) and the combined extracts dried over magnesium sulphate. After removing solvent, the product was recrystallised from benzene/hexane (1;1) to yield a pale yellow amorphous solid (1.4g) mp 128°-128.5°.

$C_{14}H_{14}O_4$ requires: C. 68.3% H. 5.7%
Found: C. 68.1% H. 5.9%

EXAMPLE 5

2-(2,3-Dihydro-2-ethyl-4-oxo-4H-1-benzopyran-6-yl)propanol 2-(2-Ethyl-4-oxo-4H-1-benzopyran-6-yl)propan-1-ol (4.1g) was taken up in ethanol (100 ml), Raney Nickel (5.0 g) was added and the mixture hydrogenated at 45 psi for 2 hours. The catalyst was removed by filtration (Hyflo supercel) and replaced with a fresh batch (5.0 g) and hydrogenation at 45 psi continued for a further 3 hours. The catalyst was removed by filtration and the filtrate evaporated to yield 2-(2,3-dihydro-2-ethyl-4-oxo-4H-1-benzopyran-6-yl)propanol as a pale green oil (4.5 g), I.R. carbonyl absorption 1690 cms$^{-1}$.

The crude product was treated with Jones reagent, as described in Example 2, affording a pale yellow oil (2.7g) which was purified by chromatography on silica gel using ether as eluant. Trituration with petroleum ether (bp 40°-60° C) afforded a white solid (1.64g) mp 75.5°-8° C.

$C_{14}H_{16}O_4$ requires: C, 67.7% H, 6.5%
Found: C, 67.7% H, 6.7%

EXAMPLE 6

2-(2,3-Dihydro-2-ethyl-4-oxo-4H-1-benzopyran-6-yl)propionic acid

Methyl-2-(4-methoxyphenyl)propionate (22.0g) was dissolved in dichloromethane (330 ml) and titanium tetrachloride (100.12g, 58 ml) was added dropwise with stirring and cooling. The temperature being maintained at −15° C to −10° C. After stirring the red-brown mixture for 10 minutes pent-2-enoylchloride (20.15g) was added, dropwise, again keeping the temperature between −15° C and −10° C. The reaction mixture was stirred until the starting material had been consumed (as shown by thin layer) chromatography silica gel: chloroform).

Boron trichloride (20 ml) was added at −15° C and the reaction mixture allowed to warm up to 5° C and poured onto a mixture of ice and concentrated hydrochloric acid and stirred vigorously for 30 minutes to ensure complete destruction of the organo metallic complexes. The dichloromethane was separated and the aqueous phase extracted with dichloromethane. The combined dichloromethane extracts were washed with sodium bicarbonate solution, dried and evaporated affording the intermediate methyl 2-[4-hydroxy-3-(pent-2-enoyl)phenyl]propionate as an oil.

The oil was taken up in ethanol (500 ml) and stirred with 10% aqueous sodium hydroxide solution (136 ml) at room temperature for 2 hours. The solution was acidified and the ethanol removed in vacuo. The aqueous residue was extracted with ether and the combined ethereal extracts were dried. The drying agent was removed by filtration. The ethereal filtrate was treated with dicyclohexylamine (21g) and the solid salt removed by filtration. The free acid was regenerated by stirring in an ether/2N hydrochloric acid (1:1) mixture for 3 hours at room temperature. The dicyclohexylamine hydrochloride was removed by filtration and the filtrate worked up for acidic material, using ether as the solvent, affording the crude product (16.9g) as a brown oil. This oil was recrystallised from ether/hexane to yield the desired product (10.3g) mp 74°-5° C.

EXAMPLE 7

2-(2,3-Dihydro-2-isopropyl-4-oxo-4H-1-benzopyran-6-yl) propionic acid a. Methyl 2-(3-acetyl-4-hydroxyphenyl)propionate

Titanium tetrachloride (82.3 mls) was added dropwise to a stirred solution of methyl 2-(4-methoxyphenyl)propionate (25g) in dry dichloromethane (250 mls), cooled in an ice/salt-bath, at a rate sufficient to maintain the temperature between −10° C and −5° C. The mixture was stirred for 10 minutes and acetyl chloride (10g) was added dropwise at a rate sufficient to maintain the temperature below 0° C. The solution was stirred at −5° C for 1½ hours when boron trichloride (15 mls) was added. Stirring was continued for one half hour at +3° C before pouring on to crushed ice/concentrated hydrochloric and separating the two phases. The aqueous phase was extracted with ether (3x) and the combined organic extracts were washed with saturated sodium bicarbonate solution, saturated brine solution, and dried over anhydrous magnesium sulphate. Evaporation of the solvent yielded the crude product as a pale yellow oil. Vacuum distillation furnished a pale yellow oil bp 120°-125° C/0.15mm (16.2g; 59%)

The i.r. spectrum showed carbonyl bands at 1643 and 1735 cm$^{-1}$ b. Methyl-2-(2-isopropyl-4-oxo-4H-1-benzopyran-6-yl)propionate

Sodium hydride (18.5g;50% dispersion in oil) was washed free from oil by decantation with dry ether (3x): Methyl 2-(3-acetyl-4-hydroxyphenyl)propionate(16.2g) in dry hexamethylphosphoramide (40 mls) was added to the resulting stirred slurry at a rate sufficient to maintain the temperature between +20° C and +25° C. When evolution of hydrogen had ceased, ethyl isobutyrate (27 mls) was added dropwise at a rate sufficient to maintain the temperature between +20° C and +25° C, and the solution was stirred at room temperature overnight. Water was then added, followed by dilute hydrochloric acid and ethanol (100 mls). The solution was refluxed for 45 minutes, the ethanol was evaporated on a 'Rotavapor' and the aqueous residue was extracted with ether (3x). The combined organic extracts were washed with sodium bicarbonate solution, saturated brine solution and dried over anhydrous magnesium sulphate. Evaporation of the solvent yielded methyl 2-(2-isopropyl-4-oxo-4H-1-benzopyran-6-yl)propionate as a red oil (5.4g; 25%). The i.r. spectrum showed carbonyl bands at 1650 cm$^{-1}$ and 1730cm$^{-1}$.

c. Methyl 2-(2,3-dihydro-2-isopropyl-4-oxo-4H-1-benzopyran-6-yl) propionate

Raney Nickel (10.0g) was added to methyl 2-(2-isopropyl-4-oxo-4H-1-benzopyran-6-yl)propionate (10.7g) in dry ethanol (100 mls) and hydrogenated at 45 p.s.i. until uptake of hydrogen ceased. The Raney Nickel was filtered off and the solvent evaporated to yield the crude methyl 2-(2,3-dihydro-2-isopropyl-4-oxo-4H-1-benzopyran-6-yl) propionate as a pale green oil (9.2g; 90%).

The i.r. spectrum showed carbonyl bands at 1690cm$^{-1}$ and 1730cm$^{-1}$.

d. 2-(2,3-Dihydro-2-isopropyl-4-oxo-4H-1-benzopyran-6-yl)

Sodium bicarbonate (9.0 g) in water (100 mls) was added to a solution of methyl 2-(2,3-dihydro-2-isopropyl-4-oxo-4H-1-benzopyran-6-yl)propionate (9.0g) in ethanol (100 mls) and the mixture was refluxed overnight. The ethanol was removed on a 'Rotavapor' and the aqueous phase was washed with ether(2x), acidified with dilute hydrochloric acid and extracted with ether(3x). The combined ethereal extracts were washed with saturated brine solution, dried over anhydrous magnesium sulphate and evaporated to yield a red oil (6.8g). This red oil was taken up in ether and dicyclohexylamine (4.7g) was added. The precipitate was collected and recrystallised from ethyl acetate to yield 2-(2,3-dihydro-2-isopropyl-4-oxo-4H-1-benzopyran-6-yl)propionic acid dicyclohexylamine salt as a white crystalline solid. This solid was suspended in ether and dilute hydrochloric acid was added until no more dicyclohexylamine hydrochloride was precipitated. The solid was filtered and the solvent was evaporated to yield 2-(2,3-dihydro-2-isopropyl-4-oxo-4H-1-benzopyran-6-yl)propionic acid as a red oil (2.7g). This oil was recrystallised from ether/n-hexane(1:4) to yield 2-(2,3-dihydro-2-isopropyl-4-oxo-4H-1-benzopyran-6-yl)propionic acid as a white microcristalline solid (0.5g;5%) mp. 94°-95° C.

Found: C 68.3%; H 6.8%

$C_{15}H_{15}O_4$ requires: C 68.6%; H 6.9%

Nmr, ir and m.s. consistent with the proposed structure.

EXAMPLE 8

The following compounds were also prepared by the procedures indicated using appropriate starting materials:

a. 2-(2,3-Dihydro-4-oxo-4H-1-benzopyran-6-yl)propionic acid mp 121°-2° C

Prepared by the process of Example 5.

Starting material - 2-(4-oxo-4H-1-benzopyran-6-yl)propan-1-ol b. 2-[2,3-Dihydro-2-(prop-1-yl)-4-oxo-4H-1-benzopyran-6-yl] propionic acid mp 81°-3° C Prepared by the process of Example 5.

Starting material - 2-(2-propyl-4-oxo-4H-1-benzopyran-6-yl) propan-1-ol c. 2-(2,3-Dihydro-3-methyl-4-oxo-4H-1-benzopyran-6-yl propionic acid mp 70°-73° C Prepared by the process of Example 7.

Starting material - propionyl chloride and using ethyl formate in place of ethyl isobutyrate in step (b).

Theory for $C_{12}H_{14}O_4$: C, 66.65% H, 6.0%

Found: C, 66.6% H, 6.2% d. 2-(2,3-Dihydro-2-phenyl-4-oxo-4H-1-benzopyran-6-yl) propionic acid mp 168°-9° C Prepared by the process of Example 6.

Starting material - cinnamoyl chloride e.
2-(2,3-Dihydro-2-methyl-4-oxo-4H-1-benzopyran-6-yl) propionic acid mp 108°–9° C Prepared by the process of Example 6.
Starting material - crotonyl chloride f. 2-(2-Propyl-4-oxo-4H-1-benzopyran-6-yl)propan-1-ol Prepared by the process of Example 3(e)
I.R. carbonyl absorption at 1650cm$^{-1}$
Starting material ethyl butyrate g. 2-(4-Oxo-4H-1-benzopyran-6-yl)propan-1-ol Prepared by the process of Example 3(e)
I.R. carbonyl absorption at 1660cm$^{-1}$
Starting material ethyl formate.

We claim:

1. A method of treatment of an inflammatory condition which comprises administration of an effective amount of 2-(2,3-dihydro-2-isopropyl-4-oxo-4H-1-benzopyran-6-yl)propionic acid to a patient suffering from such a condition.

* * * * *

UNITED STATES PATENT AND TRADEMARK OFFICE
CERTIFICATE OF CORRECTION

PATENT NO. : 4,057,641

DATED : November 8, 1977

INVENTOR(S) : Richard Anthony Appleton et al.

It is certified that error appears in the above-identified patent and that said Letters Patent are hereby corrected as shown below:

Col. 7, line 52, "1660 $cm^{31\ 1}$" should read --1660 $cm^{-1}$--.

Signed and Sealed this

Twenty-third Day of May 1978

[SEAL]

Attest:

RUTH C. MASON
*Attesting Officer*

LUTRELLE F. PARKER
*Acting Commissioner of Patents and Trademarks*